United States Patent [19]

Kawai et al.

[11] 4,456,513
[45] Jun. 26, 1984

[54] METHOD OF AND APPARATUS FOR MEASURING ELECTROPHORETIC MOBILITY

[76] Inventors: Yoshio Kawai, 3-12-10 Kichijoji-Higashicho, Musashino-shi, Tokyo; Toshiharu Shirakami, 3-41-11 Narusedai, Machida-shi, Tokyo, both of Japan

[21] Appl. No.: 411,282

[22] Filed: Aug. 25, 1982

[30] Foreign Application Priority Data

Sep. 10, 1981 [JP] Japan .................. 56-143016

[51] Int. Cl.³ .................. B01D 57/02; C25B 7/00
[52] U.S. Cl. .................. 204/180 R; 204/299 R;301
[58] Field of Search .................. 204/299 R, 301, 180 G, 204/180 R, 195 R

[56] References Cited

U.S. PATENT DOCUMENTS

| | | | |
|---|---|---|---|
| 3,454,487 | 7/1969 | Riddick | 204/299 R |
| 3,723,712 | 3/1973 | Kromline, Sr. et al. | 235/151.31 |
| 3,764,512 | 10/1973 | Greenwood et al. | 204/299 R |
| 3,909,380 | 9/1975 | Day et al. | 204/180 R |
| 4,046,667 | 9/1977 | Goetz | 204/299 R |

Primary Examiner—Howard S. Williams
Assistant Examiner—T. F. Chapman

[57] ABSTRACT

In the method of and apparatus for measuring the electrophoretic mobility, the electrophoretic mobility for the particles in a test sample is determined by measuring the apparent electrophoretic mobility at the positions for each of a plurality of different particles contained in the test sample moving under the electric field, and substituting the position for the stationary plane at which the flow velocity due to electroosmotic effect is zero into the theoretical curve $(M(x) = -FX^2 + AX + B$ based on the measured data.

4 Claims, 4 Drawing Figures

METHOD OF AND APPARATUS FOR MEASURING ELECTROPHORETIC MOBILITY

BACKGROUND OF THE INVENTION

This invention concerns a method of and apparatus for measuring the electrophoretic mobility.

Charged particles in an electrolyte solution migrate toward an anode or a cathode in the solution when they are applied with an electric field, and such phenomenon, i.e., electrophoresis can be utilized for the understanding of some properties of the solute particles since the charged particles migrate at a velocity inherent to the particles under constant external conditions. The electrophoresis, together with the electroosmosis and the like, belong to interfacial electrokinetic phenomena and electrophoretic apparatus, for instance, observing the movement of charged colloidal particles are well-known in the field relevant to surface charged minute substances as the apparatus for measuring the interfacial electrokinetic phenomena. Such electrophoretic apparatus have recently attracted attention also in the immunological field as effective means for obtaining various immunological information from the electrokinetic phenomena of leucocytic immune-cells in bloods, for instance.

The electrophoretic apparatus generally comprises a cuvette (measuring cell), an electrode vessel having electrodes, a thermostatic bath, an electrical power source and an electrophoretic mobility detector. The electrophoretic apparatus can determine the properties and the charged states of particles which are dispersed in an electrolyte solution placed in the cuvette as a medium for the electrophoresis, by applying a DC voltage between the electrodes to generate an electric field and measuring the velocity of the charged particles that migrate in the cuvette in accordance with the electric field thus applied. Electrophoretic mobility of the particles is determined on the basis of the moving velocity (V) of the particle and the intensity of the electric field (E), and the electrophoretic mobility thus determined can be expressed by the moving velocity of each of the particles per intensity of the electric field, that is, $\mu$/sec per V/cm.

By the way, upon measurement of the electrophoretic mobility, electroosmotic effect of the medium caused by the electrical charging on the cuvette has to be taken into consideration. In usual electrophoretic apparatus, the cuvette is generally made of glass material in view of the optical property, accuracy in the fabrication, easy of washing and the like and, since the cuvette is charged negatively as will be apparent from the chemical structure of glass, the medium (electrolyte for electrophoresis) in the cuvette attains an electrical equilibrium at a high positive ion concentration near the wall of the vessel. Accordingly, when an electric field is applied for electrophoresis on both sides of the cuvette in such a state, electroosmotical medium flow occurs along the wall together with the electrophoretic migration of the particles. Thus, the electrophoretic mobility actually measured for the particles is the apparent electrophoretic mobility, that is, the mathematical sum of the true electrophoretic mobility and the flow rate of the medium caused by the electroosmosis. In view of the above, only the particles situated on a position where the electroosmotic flow velocity is zero, that is, on a theoretical stationary plane have been selected as the object to be measured in the prior method employed so far for determining the true electrophoretic mobility. However, since the possibility that the particles situate on the theoretical stationary plane is extremely low and only a restricted portion of the particles contained in the test specimen can been measured in the prior method, it worsens the measuring efficiency and brings about a difficulty in the statistical analysis of the test specimen. Further, it is not always certain whether the particles situated on the stationary plane are being measured or not as described later.

SUMMARY OF THE INVENTION

Accordingly, one object of this invention is to eliminate the foregoing drawbacks in the prior art and to provide a method of measuring the electrophoretic mobility which comprises measuring the position $X_j$ (distance from inner front face of the cuvette) for each of the particles contained in a test sample, applying an electric field to the test sample to measure the apparent electrophoretic mobility $M_j$ at the position $X_j$ for each of the particles, and substituting the position for the stationary plane at which the flow velocity due to the electroosmotic effect is zero into the theoretical curve $M(x) = -FX^2 + AX + B$ on the basis of the position $X_j$ and the apparent electrophoretic mobility $M_j$ for the measured particles to determine the true electrophoretic mobility for the particles.

Another object of this invention is to provide an apparatus for measuring the electrophoretic mobility, for practicing the above method, which comprises means for measuring the position $X_j$ for each of the particles contained in a test sample, means for applying an electric field to the test sample to measure the apparent electrophoretic mobility $M_j$ at the position $X_j$ for each of the particles, and means for substituting the position for the stationary plane at which the flow velocity due to the electroosmotic effect is zero into the theoretical curve $M(x) = -FX^2 + AX + B$ on the basis of the position $X_j$ and the apparent electrophoretic mobility $M_j$ for the measured particles to determine the true electrophoretic mobility for the particles.

According to this invention, since the true electrophoretic mobility is determined by measuring the apparent electrophoretic mobility $M_j$ at each of a plurality of different positions $X_j$ for the particles contained in the test specimen under the application of an electric field and on the basis of the theoretical curve $M(x)$ from the apparent electrophoretic mobility $M_j$ at each of the different positions $X_j$ with respect to the particles situated at each of the positions in a wide range as the object for the measurement, the electrophoretic mobility thus determined is highly reliable and the measuring efficiency can be improved significantly. Further, since the theoretical curve is determined from the apparent electrophoretic mobility at each of a plurality of different positions in a wide range and the true position on the theoretical plane is determined based on the theoretical curve in the method of this invention, the determination is highly reliable. Furthermore, since all the particles in the cuvette can be objects for measurement, satisfactory measurement is enabled even for the test specimen containing comparatively small number of particles. According to this invention, easy and accurate statistical analysis can be carried out even for immuno-cells in which the electrophoretic mobilities for individual particles are scattered greatly, and much contribution can be expected for the design and manufacture of diagnostic instruments and apparatus.

DETAILED DESCRIPTION OF A PREFERRED EMBODIMENT

Figure 1:
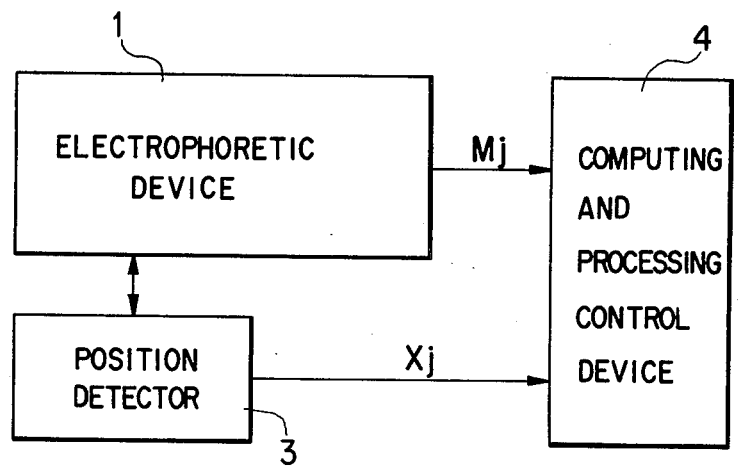
FIG. 1 is a block diagram for the constitution of a preferred embodiment of an apparatus for measuring the electrophoretic mobility according to this invention.

Referring to FIG. 1, the apparatus for measuring the electrophoretic mobility for achieving this invention method comprises an electrophoretic device 1, a position detector 3 for measuring the position Xj for each particle and a computing and processing control device 4 which is supplied at its input with the position Xj for particle outputted from the position detector 3 and the apparent electrophoretic mobility Mj at the position Xj outputted from the electrophoretic device 1, determines a theoretical curve: $M(x) = -FX^2 + AX + B$ from the position Xj and the apparent electrophoretic mobility Mj and further determines therefrom the true electrophoretic mobility for the particles.

Figure 2:
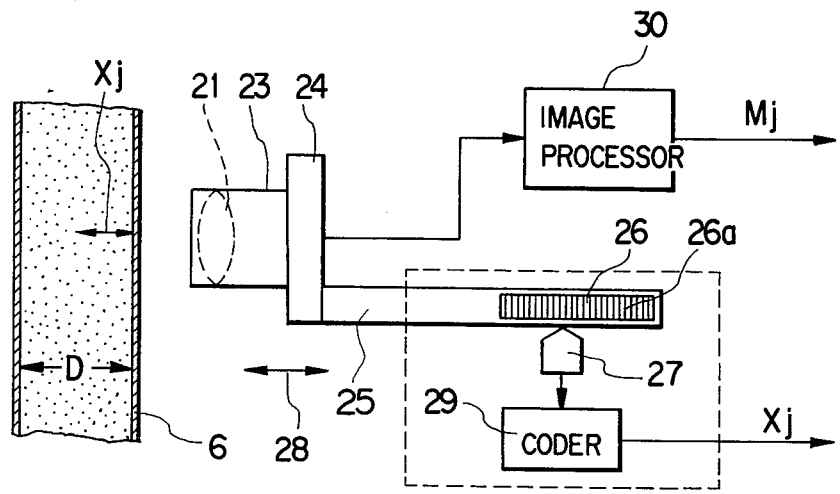
FIG. 2 is a schematic view for the constitution showing an example of a position detector for use in the apparatus for measuring the electrophoretic mobility shown in FIG. 1.

Referring to FIG. 2, the position detector 3 for use in the apparatus for measuring the electrophoretic mobility utilizes an auto-focusing microscope for measuring the position Xj for each particle in a cuvette 6. An objective 21 of the microscope is disposed in approximation to the cuvette 6. A rod member 25 is mounted on a flange 24 of a lens holder 23 which holds the objective 21. The rod member 25 carries a magnetic tape 26. A magnetic senser 27 is disposed close to the magnetic tape 26, of which an output signal is produced through a coder 29 as the position signal Xj. In such an auto-focusing microscope, the objective 21 moves in the direction shown by the arrow 28 so as to detect the particle within the cuvette 6. When the objective is focused on a particle which is located at a position Xj, the movement of the objective 21 is stopped. At the same time, as the objective 21 moves to detect the particle in focus, the magnetic tape 26 moves in the direction shown by the arrow 28, so that the magnetic sensor 27 reads mark signals 26a which are previously recorded on the magnetic tape 26 at suitable intervals the coder 29 produces the position Xj of the particle on the basis of the number of the mark signals 26a read from the magnetic tape 26 and the interval between the mark signals. Further, after the position Xj of the particle is determined, the image of the particle through the objective 21 is handled by an image processor 30 incorporated into the electrophoretic device 1 to produce the apparent electrophoretic mobility Mj of the particle.

Figure 3:
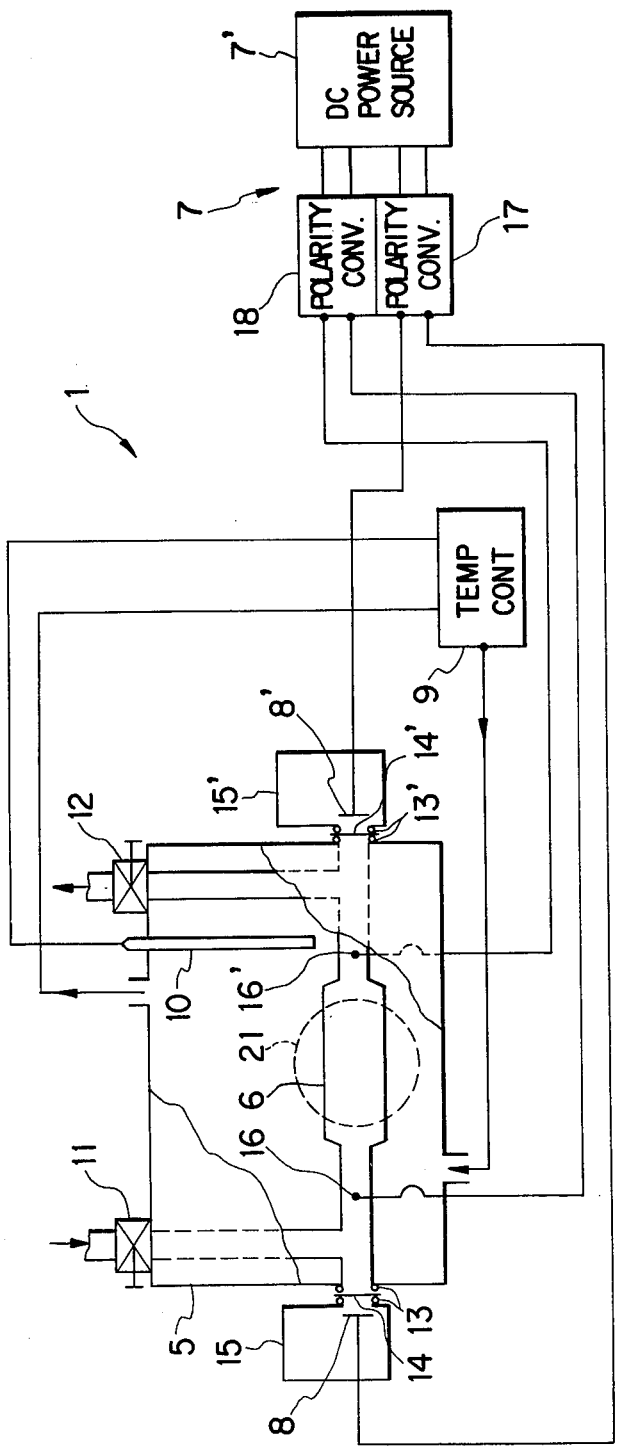
FIG. 3 is a schematic view for the constitution of a microscopic electrophoretic device for use in the apparatus for measuring electrophoretic migration rate shown in FIG. 1.
Figure 4:
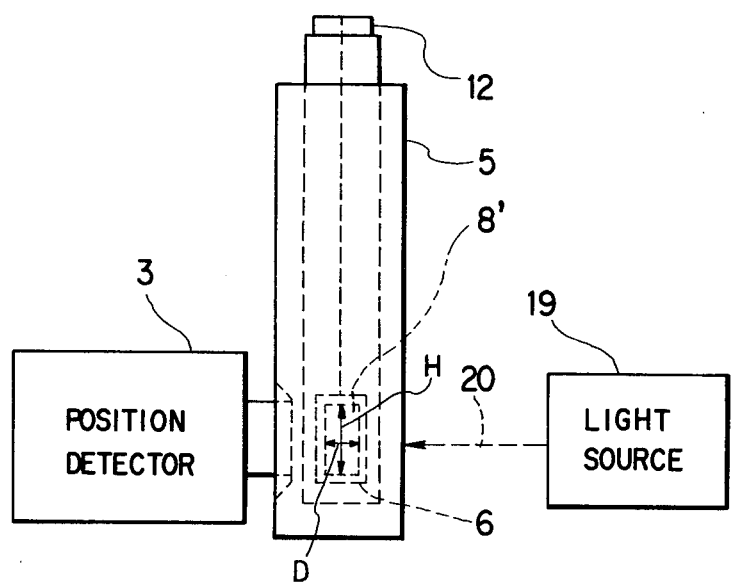
FIG. 4 is a schematic side elevational view for the microscopic electrophoretic device shown in FIG. 2.

FIG. 3 shows one example of the electrophoretic device 1, wherein a cuvette 6 containing a test sample is disposed within a thermostatic bath 5, and a sample inlet 11 and a sample outlet 12 are disposed near the both ends of the cuvette 6 by way of vertically standing glass pipes extended therefrom respectively. The thermostatic vessel 5 is equipped with a temperature control device 9 and a temperature sensor 10 so as to control the inside of the cuvette 6 at a constant temperature. The cuvette 6 is made, for example, of quartz in a square cylindrical shape with 550μ width and height/width ratio of 10. Glass tubes extended laterally from the right and left of the cylinder are opened by way of gaskets 13, 13' and separation membranes 14, 14' respectively to electrolyte vessels 15, 15' containing phosphoric acid buffer, and electrodes 8, 8' are disposed within the electrolyte vessels 15, 15'. The electrodes 8, 8' are connected respectively to a polarity converter 17 of a power source 7. A DC voltage from a power source 7' capable of setting a DC voltage Vb is supplied to the electrodes 8, 8' to thereby apply an electric field to the test sample contained in the cuvette 6. A pair of platinum voltage detection probes 16, 16' are disposed in the flow passage of the cuvette 6 and a voltage Va detected between the pair of platinum voltage detection probes is supplied by way of a polarity converter 18 of the power source 7 to the DC power source 7', where the detection voltage Va is controlled so that the voltage Va is equalized to the voltage Vb, that is, the voltage Va is decreased if Va > Vb and increased if Va < Vb. In order to reduce the scattering for the values in the measurement of electrophoresis, the polarities converters 17, 18 are designed such that the measurement can be repeated for several times while alternating the polarity of the voltage applied to the electrodes on every measurement. In such an electrophoretic device described above, there is utilized an image processor or means 30 for measuring the movement of the particle as disclosed, for example, in the U.S. Pat. No. 4,238,767. The means 30 handles the image signal concerning the particle within the cuvette 6 and obtained through the objective 21 to produce the apparent electrophoretic mobility Mj of the particle. In order to obtain a good signal-to-noise ratio of the image signal supplied to the means 30, the light 20 from a light source 19 illuminates the measuring area in the cuvette 6 as shown in FIG. 4. The partition membranes 14, 14' serve to avoid the effects of gases evolved upon electrolysis at the electrodes 8, 8' on the electrophoresis of the particles to be measured.

Reference will now be made to the operation of the apparatus for measuring the electrophoretic mobility and the method of measuring the electrophoretic mobility according to this invention.

In using this apparatus, a sample is at first supplied to the inside of the cuvette 6 by opening the sample inlet 11 and the sample outlet 12 and the temperature within the thermostatic vessel 5 is controlled by the temperature control device 9 for the thermostatic vessel 5. When the temperature is settled, a DC voltage is supplied from the power source 7 to the electrodes 8, 8' in such a way that the voltage between the voltage detection probes 16, 16' is constant. In this case, the detection voltage from the voltage detection probes 16, 16' is converted with respect to its polarity in the polarity converter 18 before supplying to the DC power source 7' so that the polarity of the voltage supplied to the DC power source 7' is unified. The DC power source 7' is designed, for example, to operate at 100 V AC input and issue a maximum output of 10mA and 200 V.

When an electric field is thus applied from the electrodes 8, 8' on the sample within the cuvette 6, the particles contained in the sample migrate toward either of the electrodes 8 and 8'. Then, the electrophoretic mobility or the electrophoretic migration velocity of the moving particles is measured for each of the positions in the cuvette 6 by the position detector 3 and the electrophoretic device 1. Since the flow speed of the medium due to the electroosmotic effect is added as described previously, the electrophoretic mobility thus measured is the apparent electrophoretic migration rate. When the apparent electrophoretic velocity as the sum of the true electrophoretic velocity of the particles and the electroosmotic medium flow speed is measured for each of the positions in the cuvette 6, the distribution of the measured data for the apparent electrophoretic mobility forms a theoretical parabolic curve which is in symmetry with the approximate center of the cuvette, in the case where the cuvette 6 has a normal configuration such as a square or circular cylinder as in this embodiment.

Apparent electrophoretic mobility Mj at each position Xj for a plurality of optional particles contained in the test sample is measured respectively and the data group $[Xj, Mj]_{j=1-N}$ are collected. Since the velocity distribution of the medium flow in the square cuvette forms a parabolic curve as described above, the measured values also form a parabolic distribution in average. Then, it is assumed here that the relation between the position X and the apparent electrophoretic mobility M(x) for each of the particles as a theoretical curve with unknown parameters F, A, B, that is, as a parabolic curve is given by:

$$M(x) = -FX^2 + AX + B \quad (1)$$

and the equation (1) is stored in the computing and processing control device 4. Then, the computing and processing control device 4, when inputted with the data group $[Xj, Mj]_{j=1-N}$ measured as above, applies the data group $[Xj, Mj]_{j=1-N}$ to the above equation and determines the parameters F, A, B by using the least square method. The peak position C for the parabolic curve M(x) is at A/2F as apparent from the equation (1).

Further, the position $D_{sp}^{\pm}$ for the stationary plane where the medium flow speed due to electroosmosis is zero is given from the Komagata's formula as below:

$$D_{sp}^{\pm} = C \pm \frac{D}{2} \sqrt{\frac{1}{3} + \frac{128}{\pi^5} \cdot \frac{D}{H}} \quad (2)$$

where
 C: peak position for parabolic curve (=A/2F)
 D: width of the cuvette
 H: height of the cuvette Assuming now the true electrophoretic mobility of individual particles as mj and the mean value therefor as m, the apparent electrophoretic mobility Mj for the particle measured at the position Xj is expressed as:

$$Mj = V(Xj) + mj = V(Xj) + m + \Delta j \quad (3),$$

where V(Xj) is a medium flow velocity and $\Delta j = mj - m$.

Further, since the parabolic curve M(x) is the mean value for the apparent electrophoretic mobility $$M(Xj) = V(Xj) + m \quad (4)$$

Since the medium flow velocity at the stationary plane is expressed as $V(D_{sp}^{\pm}) = 0$, the true electrophoretic mobility mj of individual particles and the average value m therefor are induced from the equations (1), (3) and (4) as below:

$$mj = m + \Delta j = m + Mj - M(Xj) = m + Mj - [-FXj^2 + A \cdot Xj + B] \quad (5)$$

$$m = M(D_{sp}^{\pm}) = -F(D_{sp}^{\pm})^2 + A(D_{sp}^{\pm}) + B \quad (6)$$

Since the cuvette thickness D and the cuvette height H mentioned above are given to the computing and processing control device 4, the position for the stationary plane $D_{sp}^{\pm}$ is calculated from the above equation (2) and the position for the stationary plane is substituted into the equation of the parabolic curve defined by the parameters F, A and B determined as above, to determine the mean value m for the true electrophoretic mobility as in the equation (6) and also the true electrophoretic mobility mj for individual particles from the equation (5).

The sample distribution $S^2$ for the particle group determined as above is expressed as in the following equation:

$$S^2 = \sum_{j=1}^{N} [Mj - M(Xj)]^2/N - 1$$

As apparent from the above analysis for numerical values, it is not always necessary that Xj is an absolute distance from the wall surface of the cuvette but a relative distance, if it can be determined, may be compensated into the absolute distance from the calculated value for the theoretical stationary plane.

As apparent from the foregoing principle for the analysis, since the actually measured values are applied to the theoretical curve, the measurement for the electrophoretic mobility is preferably carried out uniformly from the front to the rear surfaces of the cuvette in this invention, while only the particles on the theoretical stationary plane have been taken as the object for the measurement in the prior method. In this respect, this invention is remarkably advantageous over the prior method in view of the easiness in the measurement and the improvement in the efficiency.

Further, this invention provides an extremely effective means for the measurement of electrophoretic mobility for those specimens where the number of particles to be measured is small or where the sample shows great variation in the mobility in view of the experimental restriction or the nature of the measured sample. For instance, upon measurement of these samples, it can provide such a method as at first determining the velocity distribution V(x) for the medium from the standard sample with less variation capable of prepararing a lot of test particles by using the foregoing method, setting the true electrophoretic mobility as mj=MJ-V(Xj) and then substituting the measured values for the position (Xj) and the apparent electrophoretic mobility (Mj) of the measured particles directly into the above equation.

This invention will now be explained in more detail referring to concrete examples.

The conditions for the electrophoretic experiment were as below:
Sample for electrophoresis: sheep erythrocyte
Dispersing liquid: phosphoric acid buffer solution; pH 7.2 ($15 \times 10^{-3}$ v/cm)
Temperature for electrophoresis: 24° C.

Cuvette: square cylindrical shape; width D=550 μm; height H=5500 μm.

EXAMPLE 1

Apparent electrophoretic mobilities for 20 particles were measured at each of the positions in the cuvette shown in Table 1, and the data group containing each of the positions and the average value for the apparent electrophoretic mobility for 20 particles at each of the positions were used for the numerical analysis as stated above. The results are shown in Table 1.

Since the apparent mobility is the mean value for 20 particles at each of the positions, variations among the individual particles are offset to each other to thereby correctly reflect the medium flow. The curve M(x) thus determined passes through all of the actually measured values. This means that the flow in the cuvette exactly forms a parabolic curve. By the way, since the width (D) of the cuvette is 550 μm, the center for the flow has usually been considered to be at 275 μm (550/2) but the reliable result of this data procession indicates that the center (C) is at 269 μm. This 6 μm deviation is due to the illumination method of dark field illumination. Specifically, it shows a fact that a particle is viewed as if it were "in focus" if the focal point of an object lens situates 6 μm on this side of the particle. With the deviation from 275 to 269 μm, the true position for the stationary plane is compensated from $$107\left(\frac{D}{2} - \frac{D}{2}\sqrt{1 + \frac{128}{\pi^5} \cdot \frac{D}{H}}\right) \text{ to}$$

$$101\left(C - \frac{D}{2}\sqrt{1 + \frac{128}{\pi^5} \cdot \frac{D}{H}}\right).$$

This is quite a new fact that could not be anticipated at all in the prior method. Then, m=M(101)=0.87 is obtained as the mean value for the true electrophoretic mobility of the measured particles.

TABLE 1

| | Measured value | | |
|---|---|---|---|
| | Apparent electrophoretic mobility (average for 20 | Calculated Value | |
| Position | particles) | Position (X) | M(x)* |
| 50 | 0.35 | 50 | 0.35 |
| 100 | 0.86 | 100 | 0.86 |
| 200 | 1.48 | 200 | 1.48 |
| 275 | 1.61 | 275 | 1.61 |
| 350 | 1.44 | 350 | 1.44 |
| 450 | 0.75 | 450 | 0.75 |

*Applied curve:
$M(x) = -FX^2 + AX + B$
($F = 2.62 \times 10^{-5}$, $A = 1.41 \times 10^{-2}$,
$B = -2.91 \times 10^{-1}$) Center (C) = 269 (μm)
Stationary plane:
position; 101 μm,
true electrophoretic
mobility; 0.87

EXAMPLE 2

In this experiment, apparent electrophoretic mobilities were measured successively for 20 particles at optional positions ranging from the front wall to the rear wall of the cuvette and the data group was subjected to numerical analysis. The results are shown in Table 2.

Since the measured values represent data concerning each one particle at one point, they are distributed above and below the applied curve depending on the scattering of the individual particles but the curve applied corresponding to the average values well conforms to the above experimental results (parameter error within 2%). In statistical point of view, while the previous experiment averages the measured values for 20 particles at each of the positions and provides the data exactly reflecting the medium flow, the latter experiment provides the data containing the scattering for the individual particles. However, this is an important feature of this invention that an exact profile can be determined by the measurement at most for 20 points. In this way, the true stationary plane and the true electrophoretic mobility for the individual particles can be determined at high reliability.

TABLE 2

| | Measured value | |
|---|---|---|
| Position | Apparent electrophoretic mobility | Calculated value* True electrophoretic mobility |
| 89 | 0.72 | 0.85 |
| 188 | 1.42 | 0.87 |
| 283 | 1.58 | 0.85 |
| 383 | 1.34 | 0.93 |
| 102 | 0.91 | 0.92 |
| 204 | 1.45 | 0.84 |
| 298 | 1.62 | 0.91 |
| 403 | 1.14 | 0.86 |
| 129 | 1.11 | 0.90 |
| 219 | 1.54 | 0.88 |
| 325 | 1.52 | 0.86 |
| 426 | 1.03 | 0.92 |
| 138 | 1.11 | 0.84 |
| 244 | 1.62 | 0.91 |
| 332 | 1.45 | 0.81 |
| 438 | 0.88 | 0.86 |
| 165 | 1.33 | 0.89 |
| 262 | 1.59 | 0.86 |
| 355 | 1.45 | 0.90 |
| 465 | 0.61 | 0.85 |

*Applied curve:
$M(x) = -FX^2 + AX + B$
($F = 2.58 \times 10^{-5}$, $A = 1.40 \times 10^{-2}$,
$B = -2.91 \times 10^{-1}$)
Center (C) = 271 (μm)
Stationary plane:
position; 103 μm
true electrophoretic
mobility; 0.87

In this invention, particles contained in the test sample include particles not only of spherical or circular shape but also those of any other shapes. Further, they include all kinds of charged particles, for example, those charged particles relevant to living body such as leucocytes, erythrocytes, cells (cancer cell), testis sperma, as well as bacteria, algae, fungi, heavy metal particles (for example, $TiO_2$) and the likes.

Further, the theoretical curve may be determined each measurement of the position Xj and the apparent electrophoretic mobility Mj for each of the particles to determine the true electrophoretic mobility by substituting the position of the stationary plane into the theoretical curve. However, in the case where the shape and the dimension of the cuvette are the same, if the theoretical curve is once determined by the first measured data Xj and Mj for each of the particles, it is not necessary to determine the theoretical curve each measurement of the position Xj and the apparent electrophoretic mobility Mj for each of the particles.

What is claimed is:

1. A method of measuring the electrophoretic mobility of particles, comprising measuring the position $X_j$ for each of the particles contained in a test sample, applying an electric field to the test sample to measure the apparent electrophoretic mobility $M_j$ at the position $X_j$ for each of the particles, and substituting the position for the stationary plane at which the flow velocity due to the electroosmotic effect is zero into the theoretical curve $M(x) = -FX^2 + AX + B$ on the basis of the position $X_j$ and the apparent electrophoretic mobility $M_j$ for the measured particles to determine the true electrophoretic mobility for the particles.

2. A method according to claim 1, wherein the theoretical curve $M(x) = -FX^2 + AX + B$ is determined by the position $X_j$ and the apparent electrophoretic mobility $M_j$ for the measured particles.

3. An apparatus for measuring the electrophoretic mobility of particles, comprising means for measuring the position $X_j$ for each of the particles contained in a test sample, means for applying an electric field to the test sample to measure the apparent electrophoretic mobility $M_j$ at the position $X_j$ for each of the particles, and means for substituting the position for the stationary plane at which the flow velocity due to the electroosmotic effect is zero into the theoretical curve $M(x) = -FX^2 + AX + B$ on the basis of the position $X_j$ and the apparent electrophoretic mobility $M_j$ for the measured particles to determine the true electrophoretic mobility for the particles.

4. An apparatus according to claim 3, wherein the theoretical curve $M(x) = -FX^2 + AX + B$ is determined by the position $X_j$ and the apparent electrophoretic mobility $M_j$ for the measured particles.

* * * * *

UNITED STATES PATENT AND TRADEMARK OFFICE
CERTIFICATE OF CORRECTION

PATENT NO. : 4,456,513
DATED : June 26, 1984
INVENTOR(S) : Yoshio Kawai et al.

It is certified that error appears in the above—identified patent and that said Letters Patent is hereby corrected as shown below:

On the title page add:

[73] Assignee: Kureha Kagaku Kogyo Kabushiki Kaisha, Tokyo, Japan

Signed and Sealed this

Second Day of April 1985

[SEAL]

Attest:

DONALD J. QUIGG

Attesting Officer

Acting Commissioner of Patents and Trademarks